US006933131B2

(12) United States Patent
Adamczewski et al.

(10) Patent No.: US 6,933,131 B2
(45) Date of Patent: Aug. 23, 2005

(54) NUCLEIC ACIDS ENCODING INSECT ACETYLCHOLINE RECEPTOR SUBUNITS

(75) Inventors: Martin Adamczewski, Köln (DE); Nadja Oellers, Köln (DE); Thomas Schulte, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/303,232

(22) Filed: Apr. 30, 1999

(65) Prior Publication Data

US 2002/0006657 A1 Jan. 17, 2002

(30) Foreign Application Priority Data

May 4, 1998 (DE) .................................... 198 19 829

(51) Int. Cl.[7] .................................................. C12P 21/06
(52) U.S. Cl. ................ 435/69.1; 435/320.1; 435/252.3; 435/252.33; 435/325; 536/23.5
(58) Field of Search ............................ 435/69.1, 320.1, 435/252.3, 252.33, 325; 536/23.5, 24.1, 23.2, 24.2

(56) References Cited

U.S. PATENT DOCUMENTS

| | | | |
|---|---|---|---|
| 5,591,590 A | 1/1997 | Heinemann et al. | 435/7.1 |
| 5,599,709 A | 2/1997 | Lindstrom et al. | 435/252.3 |
| 5,683,912 A | 11/1997 | Elgoyhen et al. | 435/252.3 |
| 5,693,492 A | 12/1997 | Cully et al. | 435/69.1 |

FOREIGN PATENT DOCUMENTS

WO 96/41876 12/1996

OTHER PUBLICATIONS

Ausubel, F.M. et al. Short Protocols in Molecular Biology, 3rd Edition. John Wiley and Sons, Inc. p. a–1, 1995.*
Frommel, C. et al. An Estimate on the Effect of Point Mutation and Natural Selection on te Rate of Amino Acid Replacement in Proteins. Journal of Molecular Evolution 21:233–257, 1985.*
Ngo, J.T. et al. Computational Complexity, Protein Structure Prediction, and the Levinthal Paradox in The Protein Problem and Tertiary Structure Prediction, Merz, ed., Birkhauser, Boston. pp. 491–495, 1994.*
Bowie, J.U. et al. Deciphering the Message in Protein Sequences: Tolerance to Amino Acid Substitutions. Science 247;1306–1310, 1990.*
Vogel, R, et al. Genbank Direct Submission. Accession No. Z97178, Jun. 1997.*
Liao, E.C. et al. Genbank Direct Submission. Accession No. AF045432, Jan. 1998.*
Celniker, S.E. et al. Genbank Direct Submission. Accession No. AC004326, Mar. 1998.*
Schulte, T. et al. Genbank Direct Submission. Accession No. AF143847, Apr. 1999.*
Schulte, T. et al. Genbank Direct Submission. Accession No. AF143846, 1995.*
European Journal of Neuroscience, vol. 10, pp. 879–889, 1998, Helen M. Eastham et al, Characterization of a nicotinic acetylcholine receptor from insect Manduca sexta, month unavailable.
Proc. Natl. Acad. Sci, vol. 80, pp. 2067–1073, Apr. 1983, Devillers–Thiery et al, Complete mRNA coding sequence of the acetylcholine binding α–subunit of Torpedo marmorata acetylcholine receptor: A model for the transmembrane organization of polypeptide chain.
Science, vol. 240, Wada et al, pp. 330–334, Functional Expression of a New Pharmacological Subtype of Brain Nicotinic Acetylcholine Receptor, Apr. 15, 1998.
Neuron, vol. 5, Jul. 1990, pp. 35–48, Schoepfer et al, Brain α–Bungarotoxin Binding Protein cDNAs and MAbs Reveal Subtypes of This Branchof the Ligand–Grated Ion Channel Gene Superfamily.
Molecular Neurobiology, Cockcroft et al, vol. 4, 1990, pp. 130–169 Ligand–Gated Ion Channels, month unavailable.
Journal of Neurochemistry, Schulz et al, 1998, pp. 853–862, Dα3, a New Functional αSubunit of Nicotinic Acetylcholine Receptor from Drosophila, month unavailable.
Schulz et al, unpublished, EMBL Accession No. Y15593, Jan. 22, 1999.
Stetzer et al, unpublished, EMBL Nos. AJ000390, AJ000391, AJ000392, AJ000393, Jul. 30, 1998.
Sgard et al, unpublished EMBL Nos. X81887 and X81888, Jan. 8, 1997.
Genbank, Accession No. AA540687 Jun. 2, 1997, AA698155 Dec. 18, 1997, AA697710 Dec. 18, 1997, AA697326 Dec. 18, 1997.
The EMBO Journal, vol. 7, No. 3, pp. 611–618, 1988, Bossy et al, Conservation of neural nicotinic acetylcholine receptors from Drosophila to vertebrate central nervous systems, month unavailable.
J. Insect. Physiol. vol. 33, No. 11, pp 771–790, 1987, Breer et al, Molecular Properties and Functions of Insect Acetycholine Receptors, month unavailable.
The Journal of Experimental Biology 200, pp. 2685–2692 1997, S.D. Buckingham et al, Imidacloprid Actions on Insect Neuronal Acetylcholine Receptors, month unavailable.
Quarterly Reviews of Biophysics 25, 4 1992 pp. 395–432, Jean–Pierre Changeuex et al, The functional architecture of the acetylcholine nicotinic receptor explored by affinity labelling and site–directed mutagenesis, month unavailable.

(Continued)

Primary Examiner—Dave Trong Nguyen
Assistant Examiner—Richard Schnizer
(74) Attorney, Agent, or Firm—Richard E.L. Henderson; Raymond J. Harmuth

(57) ABSTRACT

The invention relates to nucleic acids which encode insect acetylcholine receptor subunits, to the corresponding polypeptides, and to processes for discovering novel active compounds for plant protection.

16 Claims, 1 Drawing Sheet

OTHER PUBLICATIONS

Nucleic Acids Research, vol. 12, No. 1, 1984, John Devereux et al, A comprehensive set of sequence analysis programs for the VAX, month unavailable.

Proc. Natl. Aca. Sci., vol. 80, pp 1111–1115, Feb. 1983, Toni Claudio et al, Nucleotide and deduced amino acid sequences of Torpedo california acetylcholine receptor γ subunit.

The Journal of Biological Chemistry, vol. 260, No. 6, Mar. 25, 1985, pp. 3440–3450, Grzegorz Grynkiewicz et al, A new Generation of $Ca^{2+}$ Indicators with Greatly Improved Fluorescence Properties.

Proc. Natl. Acad. Sci., vol. 94, May 1997, pp. 5195–5200, P element insertion–dependent gene activation in the Drosophila eye, Bruce A. Hay et al.

EMBO Journal, vol. 5, No. 7, pp. 1503–1508, 1986, Irmgard Hermans–Borgmeyer et al, Primary structure of a developmentally regulated nicotinic acetylcholine receptor protein from Drosophila, month unavailable.

EMBO Journal, vol. 9, No. 13, pp. 4391–4398, 1990, John Marshall et al, Sequence and functional expression of a single α subunit of an insect nicotinic acetylcholine receptor, month unavailable.

BioTechniques, vol. 23, No. 1, Jul. 1997, Efficient Non–PCR–Medicated Overlap Extension of PCR Fragments by Exonuclease "End Polishing".

Nature, vol. 299, Oct. 28, 1982, pp. 793–797, Noda et al, Primary structure of α–subunit precursor of Torpedo californica acetylcholine receptor deduced from CDNA sequence.

Nature, vol. 301, Jan. 20, 1983, pp. 251–255, Noda et al, Primary structures of β– and δ–subunit precursors or Torpedo californica acetylcholine receptor deduced from cDNA sequences.

Nature, vol. 302, Apr. 7, 1983, pp. 528–532, Noda et al, Structural homology of Torpedo californica acetylcholine recrptor subunits.

FEBS, vol. 273, Nos. 1,2, pp. 177–181, Oct. 1990, SBD, a novel structural subunit of the Drosophila nicotinic acetylcholine receptor, shares its genomic localization with two α–subunits.

TINS, vol. 18, No. 3, 1995, pp. 121–127 (Perspectives) Ortells et al, Evolutionary history of the ligand–gated ion–channel superfamily of receptors, month unavailable.

The Tc1/mariner Transposon Family, pp. 126–143, Curr. Top. Microbiol. Immunol. 1996 vol. 204.

The EMBO Journal, vol. 9, No. 9, pp. 2671–2677 1990, Erich Sawruk et al, Heterogeneity of Drosophila nicotinic acetylcholine receptors: SAD, a novel developmentally regulated α–subunit.

The EMBO Journal, vol. 7, No. 9, 1988, pp. 2889–2894, Neuronal acetylcholine receptors in Drosophila: the ARD protein is a component of a high–affinity α–bungarotoxin binding complex, Patrick Schloβ et al, month unavailable.

FEBS Letters 397 1996, pp. 39–44, Stable expression in HEK–293 cells of the rat α3/β4 subtype of neuronal nicotoinic acetylcholine receptor, Eva Stetzer et al, month unavailable.

Pflügers Arch–Eur. J. Physiol 1995, 430, pp. 340–347, Zong et al On the regulation of the express L–type calcium channel by cAMP–dependent phosphorylation, month unavailable.

* cited by examiner

NUCLEIC ACIDS ENCODING INSECT ACETYLCHOLINE RECEPTOR SUBUNITS

This application claims priority to German Application 19819829.9 filed on May 4, 1998.

The invention relates, in particular, to nucleic acids which encode insect acetylcholine receptor subunits.

BACKGROUND OF THE INVENTION

Nicotinic acetylcholine receptors are ligand-regulated ion channels which are of importance in neurotransmission in the animal kingdom. The binding of acetylcholine or other agonists to the receptor induces a transient opening of the channel and allows cations to flow through. It is assumed that a receptor consists of five subunits which are grouped around a pore. Each of these subunits is a protein which consists of an extracellular N-terminal moiety followed by three transmembrane regions, an intracellular moiety, a fourth transmembrane region and a short extracellular C-terminal moiety (Changeux et al. 1992).

Acetylcholine receptors are especially well investigated in vertebrates. In this context, three groups can be distinguished on the basis of their anatomical location and their functional properties (conducting properties of the channel, desensitization, and sensitivity towards agonists and antagonists and also towards toxins such as α-bungarotoxin). The classification correlates with the molecular composition of the receptors. There are heterooligomeric receptors having the subunit composition $α_2βγδ$, which are found in muscle (Noda et al. 1982, Claudio et al. 1983, Devillers-Thiery et al. 1983, Noda et al. 1983a, b), heterooligomeric receptors which contain subunits from the α2–α6 and β2–β4 groups and which are found in the nervous system (Wada et al. 1988, Schoepfer et al. 1990, Cockcroft et al. 1991, Heinemann et al. 1997), and also homooligomeric receptors which contain subunits from the α7–α9 group and which are likewise found in the nervous system (Lindstrom et al. 1997, Elgoyhen et al. 1997). This classification is also supported by an examination of the relatedness of the gene sequences of the different subunits. Typically, the sequences of functionally homologous subunits from different species are more similar to each other than are sequences of subunits which are from different groups but from the same species. Thus, the rat muscle α subunit, for example, exhibits 78% amino acid identity and 84% amino acid similarity with that of the electric ray *Torpedo californica* but only 48% identity and 59% similarity with the rat α2 subunit (heterooligomeric, neuronal) and 36% identity and 45% similarity with the rat α7 subunit (homooligomeric, neuronal). Furthermore, the gene sequences of all the known acetylcholine receptor subunits are to a certain extent similar not only to each other but also to those of some other ligand-regulated ion channels (e.g. the serotonin receptors of the 5HT$_3$ type, the GABA-regulated chloride channels and the glycine-regulated chloride channels). It is therefore assumed that all these receptors are descended from one common precursor and they are classified into one supergene family (Ortells et al. 1995).

In insects, acetylcholine is the most important excitatory neurotransmitter of the central nervous system. Accordingly, acetylcholine receptors can be detected electrophysiologically in preparations of insect central nervous system ganglia. The receptors are detected both in postsynaptic and presynaptic nerve endings and in the cell bodies of interneurones, motor neurones and modulatory neurones (Breer et al. 1987, Buckingham et al. 1997). Some of the receptors are inhibited by α-bungarotoxin while others are insensitive (Schloβ et al. 1988). In addition, the acetylcholine receptors are the molecular point of attack for important natural (e.g. nicotine) and synthetic insecticides (e.g. chloronicotinyls).

The gene sequences of a number of insect nicotinic acetylcholine receptors are already known. Thus, the sequences of five different subunits have been described in *Drosophila melanogaster* (Bossy et al. 1988, Hermanns-Borgmeyer et al. 1986, Sawruk et al. 1990a, 1990b, Schulz et al. Unpublished, EMBL accession number Y15593), while five have likewise been described in *Locusta migratoria* (Stetzer et al. unpublished, EMBL accession numbers AJ000390–AJ000393), one has been described in *Schistocerca gregaria* (Marshall et al. 1990), two have been described in *Myzus persicae* (Sgard et al. unpublished, EMBL accession number X81887 and X81888), and one has been described in *Manduca sexta* (Eastham et al. 1997). Furthermore, a number of partial gene sequences from *Drosophila melanogaster* have been characterized as so-called expressed sequence tags (Genbank accession numbers AA540687, AA698155, AA697710, AA697326). The fact that individual sequences are very similar to those from other insects suggests that these subunits are functional homologues.

BRIEF SUMMARY OF THE INVENTION

It is of great practical importance to make available new insect acetylcholine receptor subunits, for example for the purpose of searching for novel insecticides, with those subunits which differ from the known subunits to a greater extent than is the case between functional homologues being particularly of interest.

The present invention is consequently based, in particular, on the object of making available nucleic acids which encode novel insect acetylcholine receptor subunits.

This object is achieved by the provision of nucleic acids which comprise a sequence selected from (a) the sequences according to SEQ ID NO: 1, SEQ ID NO: 3 or SEQ ID NO: 5, (b) part sequences of the sequences defined in (a) which are least 14 base pairs in length, (c) sequences which hybridize to the sequences defined in (a) in 2×SSC at 60° C., preferably in 0.5×SSC at 60° C., particularly preferably in 0.2×SSC at 60° C. (Sambrook et al. 1989), (d) sequences which exhibit at least 70% identity with the sequences defined in (a), between position 1295 and position 2195 in the case of SEQ ID NO: 1, or between position 432 and position 1318 in the case of SEQ ID NO: 3, or between position 154 and position 1123 in the case of SEQ ID NO: 5, (e) sequences which are complementary to the sequences defined in (a), and (f) sequences which, because of the degeneracy of the genetic code, encode the same amino acid sequences as the sequences defined in (a) to (d).

The degree of identity of the nucleic acid sequences is preferably determined using the GAP program from the GCG program package, Version 9.1 with standard settings (Devereux et al. 1984).

DETAILED DESCRIPTION OF THE INVENTION

Figure 1:
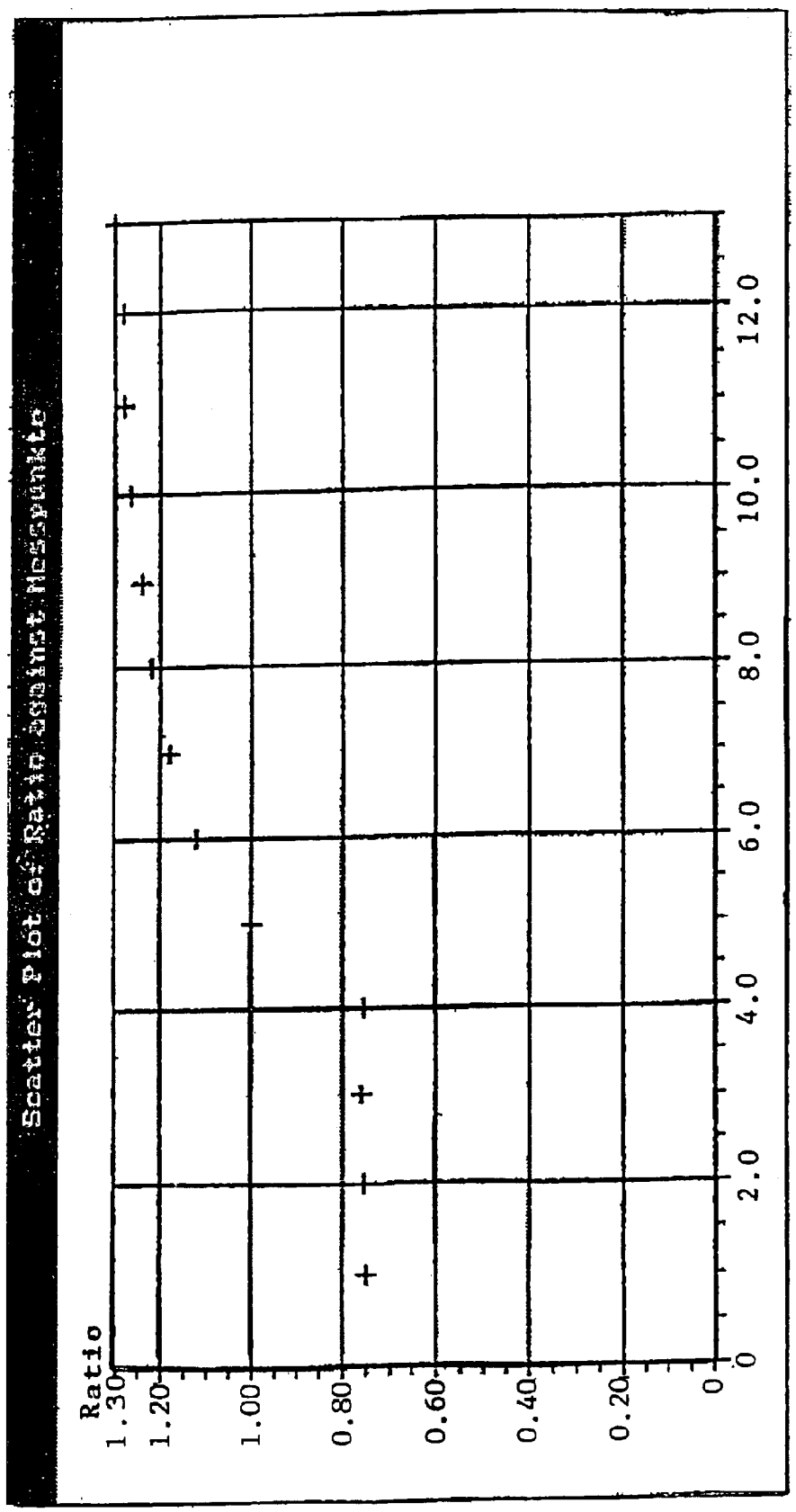
FIG. 1 is a graph illustrating the increase in intracellular calcium that occurs in cells which have been recombinantly modified as described in Example 2.

The present invention is based on the surprising finding that insects possess genes which encode subunits of, in particular, homooligomeric acetylcholine receptors.

The invention furthermore relates to vectors which contain at least one of the novel nucleic acids. All the plasmids, phasmids, cosmids, YACs or artificial chromosomes which are used in molecular biological laboratories can be used as vectors. These vectors can be linked to the usual regulatory sequences for the purpose of expressing the novel nucleic acids. The choice of such regulatory sequences depends on whether prokaryotic or eukaryotic cells, or cell-free systems, are used for the expression. The SV40, adenovirus or cytomegalovirus early or late promoter, the lac system, the trp system, the main operator and promoter regions of phage lambda, the control regions of the fd coat protein, the 3-phosphoglycerate kinase promoter, the acid phosphatase promoter and the yeast α-mating factor promoter are examples of expression control sequences which are particularly preferred.

In order to be expressed, the nucleic acids according to the invention can be introduced into suitable host cells. Both prokaryotic cells, preferably *E. coli*, and eukaryotic cells, preferably mammalian or insect cells, are suitable for use as host cells. Other examples of suitable unicellular host cells are: *Pseudomonas, Bacillus, Streptomyces*, yeasts, HEK-293, Schneider S2, CHO, COS1 and COS7 cells, plant cells in cell culture and also amphibian cells, in particular oocytes.

The present invention also relates to polypeptides which are encoded by the nucleic acids according to the invention and also the acetylcholine receptors, preferably homooligomeric acetylcholine receptors, which are synthesized from them.

In order to prepare the polypeptides which are encoded by the nucleic acids according to the invention, host cells which contain at least one of the nucleic acids according to the invention can be cultured under suitable conditions. After that, the desired polypeptides can be isolated from the cells or the culture medium in a customary manner.

The invention furthermore relates to antibodies which bind specifically to the above-mentioned polypeptides or receptors. These antibodies are prepared in the customary manner. For example, such antibodies can be produced by injecting a substantially immunocompetent host with a quantity of an acetylcholine receptor polypeptide, or a fragment thereof, according to the invention which is effective for producing antibodies, and subsequently isolating these antibodies. Furthermore, an immortalized cell line which produces monoclonal antibodies can be obtained in a manner known per se. Where appropriate, the antibodies can be labelled with a detection reagent. Preferred examples of such a detection reagent are enzymes, radioactively labelled elements, fluorescent chemicals or biotin. Instead of the complete antibody, use can also be made of fragments which possess the desired specific binding properties.

The nucleic acids according to the invention can be used, in particular, for producing transgenic invertebrates. These latter can be employed in test systems which are based on an expression of the receptors according to the invention, or variants thereof, which differs from that of the wild type. In addition, this includes all transgenic invertebrates in which a change in the expression of the receptors according to the invention, or their variants, occurs as the result of modifying other genes or gene control sequences (promoters).

The transgenic invertebrates are produced, for example, in *Drosophila melanogaster* by means of P element-mediated gene transfer (Hay et al., 1997) or in *Caenorhabditis elegans* by means of transposon-mediated gene transfer (e.g. using Tc1, Plasterk, 1996).

The invention also consequently relates to transgenic invertebrates which contain at least one of the nucleic acid sequences according to the invention, preferably to transgenic invertebrates of the species *Drosophila melanogaster* or *Caenorhabditis elegans*, and to their transgenic progeny. Preferably, the transgenic invertebrates contain the receptors according to the invention in a form which differs from that of the wild type.

The nucleic acids according to the invention can be prepared in the customary manner. For example, the nucleic acid molecules can be synthesized entirely chemically. In addition, only short segments of the sequences according to the invention can be synthesized chemically and these oligonucleotides can be labelled radioactively or with a fluorescent dye. The labelled oligonucleotides can be used to screen cDNA libraries prepared from insect mRNA. Clones which hybridize to the labelled oligonucleotides ("positive clones") are selected for isolating the relevant DNA. After the isolated DNA has been characterized, the nucleic acids according to the invention are readily obtained.

The nucleic acids according to the invention can also be prepared by means of PCR methods using chemically synthesized oligonucleotides.

The nucleic acids according to the invention can be used for isolating and characterizing the regulatory regions which occur naturally adjacent to the coding region. Consequently, the present invention also relates to these regulatory regions.

The nucleic acids according to the invention can be used to identify novel active compounds for plant protection, such as compounds which, as modulators, in particular as agonists or antagonists, alter the conducting properties of the acetylcholine receptors according to the invention. For this, a recombinant DNA molecule, which encompasses at least one nucleic acid according to the invention, is introduced into a suitable host cell. The host cell is cultured, in the presence of a compound or a sample which comprises a multiplicity of compounds, under conditions which permit expression of the receptors according to the invention. A change in the receptor properties can be detected, as described below in Example 2. Using this approach, it is possible to discover insecticidal substances.

The nucleic acids according to the invention also make it possible to discover compounds which bind to the receptors according to the invention. These compounds can likewise be used as insecticides on plants. For example, host cells which contain the nucleic acid sequences according to the invention and express the corresponding receptors or polypeptides, or the gene products themselves, are brought into contact with a compound or a mixture of compounds under conditions which permit the interaction of at least one compound with the host cells, receptors or the individual polypeptides.

Host cells or transgenic invertebrates with contain the nucleic acids according to the invention can also be used to discover substances which alter the expression of the receptors.

The above-described nucleic acids, vectors and regulatory regions according to the invention can additionally be used for discovering genes which encode polypeptides which are involved in the synthesis, in insects, of functionally similar acetylcholine receptors. According to the present invention, functionally similar receptors are understood as being receptors which encompass polypeptides which, while differing in their amino acid sequences from the polypeptides described in this present publication, essentially possess the same functions.

Comments on the Sequence Listing and the Figures:

SEQ ID NO: 1 shows the nucleotide sequence of the isolated Da7 cDNA, beginning with position 1 and ending with position 2886. SEQ ID NO: 1 and SEQ ID NO: 2 also show the amino acid sequences of the protein deduced from the Da7 cDNA sequence.

SEQ ID NO: 3 shows the nucleotide sequence of the isolated Hva7-1 cDNA, beginning with position 1 and ending with position 3700. SEQ ID NO: 3 and SEQ ID NO: 4 also show the amino acid sequences of the protein deduced from the Hva7-1 cDNA sequence.

SEQ ID NO: 5 shows the nucleotide sequence of the isolated Hva7-2 cDNA, beginning with position 1 and ending with position 3109. SEQ ID NO: 5 and SEQ ID NO: 6 also show the amino acid sequences of the protein deduced from the Hva7-2 cDNA sequence.

FIG. 1 shows the increase in intracellular calcium which occurs in cells which have been recombinantly modified as described in Example 2 following the addition of nicotine. Cells were loaded with Fura-2-acetoxymethyl ester (5–10 $\mu$M in serum-free minimal essential medium containing 1% bovine serum albumin and 5 mM calcium chloride), washed with Tyrode solution buffered with N-(2-hydroxyethyl)piperazine-N'-(2-ethanesulphonic acid) (5 mM HEPES) and alternately illuminated, under a fluorescence microscope (Nikon Diaphot) with light of 340 nm and 380 nm wavelength. A measurement point corresponds to a pair of video images at the two wavelengths (exposure time per image, 100 ms). The time interval between two measurement points is 3 s. After 8 images had been taken (measurement point 4.0), nicotine was added to a final concentration of 500 $\mu$M and the measurement series was continued. The fluorescence intensity of the cells when illuminated with light of 380 nm wavelength was divided by the corresponding intensity at 340 nm, thereby giving the ratio.

EXAMPLES

Example 1

Isolating the Described Polynucleotide Sequences

Polynucleotides were manipulated using standard methods of recombinant DNA technology (Sambrook, et al., 1989). The bioinformatic processing of nucleotide and protein sequences was carried out using the GCG program package Version 9.1 (GCG Genetics Computer Group, Inc., Madison Wis., USA).

Partial Polynucleotide Sequences

Sequence comparisons ("Clustalw") were used to identify regions, from which degenerate oligonucleotides were deduced by backtranslating the codons, of protein sequences from genes whose ability to form homooligomeric acetylcholine receptors was known. In all, 5 such oligonucleotide pairs were selected for the polymerase chain reaction (PCR). Only one combination (see below) gave a product both from *Heliothis* cDNA and from *Drosophila* cDNA.

RNA was isolated from whole *Heliothis* virescens embryos (shortly before hatching) using Trizol reagent (Gibco BRL, in accordance with the manufacturer's instructions). The same procedure was adopted with *Drosophila* embryos (24 h at 25° C.). 10 $\mu$g of these RNAs were employed in a first cDNA strand synthesis (Superscript Preamplification System for first cDNA strand synthesis, Gibco BRL, in accordance with the manufacturer's instructions, reaction temperature 45° C.).

Subsequently, 1/100 of the abovementioned first-strand cDNA was in each case employed in a polymerase chain reaction (PCR) using the oligonucleotides alpha7-1s: (5'-GAYGTIGAYGARAARAAYCA-3') SEQ. ID. No: 7 and alpha7-2a: (5'-CYYTCRTCIGCRCTRTTRTA-3') SEQ. ID. No: 8 (recombinant Taq DNA polymerase, Gibco BRL). The PCR parameters were as follows: Hva7-1 and Hva7-2: 94° C., 2 min; 35 times (94° C., 45 s; 50° C., 30 s; 72° C., 60 s) and also Da7: 96° C., 2 min; 35 times (96° C., 45 s; 50° C., 30 s; 72° C., 60 s). In each case, this resulted in a dectable band of approx. 0.2 kb in an agarose gel (1%), both in the case of *Drosophila* cDNA and in the case of *Heliothis* cDNA. After the DNA fragments had been subcloned by means of SrfScript (Stratagene), and their sequences had been determined, it turned out that two different DNA fragments had been amplified from *Heliothis* cDNA; these were 228-11=Hva7-1 (partial, containing 165 bp) and 228-8=Hva7-2 (partial, containing 171 bp). Only one DNA fragment was isolated from *Drosophila* cDNA; this was 248-5=Da7 (partial, containing 150 bp).

Isolating Poly A-containing RNA from *Heliothis* Virescens Tissue and Constructing the cDNA Libraries The RNA for cDNA library I was isolated from whole *Heliothis* virescens embryos (shortly before hatching) using Trizol reagent (Gibco BRL, in accordance with the manufacturer's instructions). The RNA for cDNA library II was isolated from whole head ganglia from 500 *Heliothis* virescens larvae (stages 4–5) usings Trizol reagent (Gibco BRL, in accordance with the manufacturer's instructions). The poly A-containing RNAs were then isolated from these RNAs by purifying with Dyna Beads 280 (Dynal). 5 $\mu$g of these poly A-containing RNAs were subsequently employed in constructing cDNA libraries I and II using the $\lambda$-ZAPExpress vector (cDNA Synthesis Kit, ZAP-cDNA Synthesis Kit and ZAP-cDNA Gigapack III Gold Cloning Kit, all from Stratagene). In a departure from the manufacturer's instructions, Superscript Reverse Transcriptase (Gibco BRL) was used for synthesizing the cDNA at a synthesis temperature of 45° C. In addition, radioactively labelled deoxynucleoside triphosphates were not added. Furthermore, the synthetisized cDNAs were not fractionated through the gel filtration medium contained in the kit but instead through Size Sep 400 Spun Columns (Pharmacia).

Complete Polynucleotide Sequences

Apart from the first screening round when isolating the Hva7-1 clone, all the screens were carried out using the DIG system (all reagents and consumables from Boehringer Mannheim, in accordance with the instructions in "The DIG System User's Guide for Filter Hybridization", Boehringer Mannheim). The DNA probes employed were prepared by means of PCR using digoxigenin-labelled dUTP. The hybridizations were carried out at 42° C. overnight in DIG Easy Hyb (Boehringer Mannheim). Labelled DNA was detected on nylon membranes by means of chemiluminescence (CDP-Star, Boehringer Mannheim) using X-ray films (Hyperfilm MP, Amersham). Initial partial sequencing of the isolated gene library plasmids was carried out, for identification purposes, using T3 and T7 primers (ABI Prism Dye Terminator Cycle Sequencing Kit, ABI, using an ABI Prism 310 Genetic Analyzer). The complete polynucleotide sequences in Hva7-1, Hva7-2 and Da7 were determined, as a commissioned sequencing carried out by Qiagen, Hilden, by means of primer walking using cycle sequencing.

a. Isolating the Da7 Clone $10^6$ phages from a *Drosophila melanogaster* cDNA library in $\lambda$ phages (Canton-S embryo, 2–14 hours, in Uni-ZAP XR vector, Stratagene) were screened using DIG-labelled 248-5 as the probe (in accordance with the manufacturer's (Stratagene) instructions). The maximum stringency when washing the filters was: 0.2×SSC; 0.1% SDS; 42° C.; 2×15 min. One clone (clone 432-1) was isolated whose insert had a size of 2940 bp (Da7, SEQ ID NO: 1). The largest open reading frame of this sequence begins at position 372 of the depicted sequence and ends at position 1822. The 770 amino acids polypeptide which is deduced from this (SEQ ID NO: 2) has a calculated molecular weight of 87.01 kD.

b. Isolating the Hva7-1 Clone $10^6$ phages from the *Heliothis* virescens embryo cDNA library (library I) were included in the screening. The first of three screening rounds took place using $\alpha$-$^{32}$P-labelled 228-11 DNA as the probe. The probe was hybridized to the filters in Quick-hyb (Stratagene) at 68° C. for one hour. The filters were then washed twice, for 15 min on each occasion, at room temperature in 2×SSC; 0.1% SDS and twice, for 30 min on each occassion, at 42° C. in 0.1×SSC; 0,1% SDS. Hybridized probes were detected by means of autoradiography, at −80° C. overnight, using XR X-ray films (Kodak) and employing intensifying screens (Amersham). The two further screening rounds were carried out using the DIG System (Boehringer Mannheim).

The clone 241-5, which was isolated in this screen, contained an insert of 3630 bp. This insert (Hva7-1, SEQ ID NO: 3) possesses a longest open reading frame which begins at position 335 of the depicted nucleic acid sequence and ends at position 1821. The 496 amino acids polypeptide which is deduced from this (SEQ ID NO: 4) has a calculated molecular weight of 56.36 kD.

c. Isolating the Hva7-2 Clone $10^6$ phages from the *Heliothis* virescens ganglia cDNA library (library II) were included in the screening. Dig-labelled 228-8 DNA was used as the probe. The maximum stringency when washing the filters was: 0.1×SSC; 0.1% SDS; 42° C.; 2×15 min.

The clone 241-5, which was isolated in this screen, contained an insert of 3630 bp. This insert (Hva7-2, SEQ ID NO: 5) possesses a longest open reading frame which begins at position 95 of the depicted nucleic acid sequence and ends at position 1598. The 501 amino acids polypeptide which is deduced from this (SEQ ID NO: 6) has a calculated molecular weight of 56.71 kD.

Example 2

Generating the Expression Constructs a. Da7

The sequence region from position 372 to position 2681 of SEQ ID NO: 1 was amplified by means of a polymerase chain reaction (PCR). Deoxyoligonucleotides having the sequences GCGAATTCACCACCATGAAAAATGCA-CAACTG SEQ ID. NO: 9 and CGAGACAATAATATGTG-GTGCCTCGAG SEQ ID NO: 10 were used for this. The Pfu polymerase from Stratagene was used as the DNA polymerase in accordance with the manufacturer's instructions. Following the amplification, the segment which had been generated was digested with the restriction endonucleases Eco RI and Xho I and cloned into a vector, i.e. pcDNA3.1/Zeo (Invitrogen), which had likewise been digested with Eco RI and Xho I.

b. Hva7-1

The sequence region from position 335 to position 1822 from SEQ ID NO:3 was amplified by means of a polymerase chain reaction (PCR). Deoxyoligonucleotides having the sequences GCAAGCTTACCACCATGGGAGGTA-GAGCTAGACGCTCGCAC SEQ ID NO:11 and GCCTC-GAGCGACACCATGATGTGTGGCGC SEQ ID NO:12 were used for this. The Pfu polymerase from Stratagene was used as the DNA polymerase in accordance with the manufacturer's instructions. Following amplification, the generated segment was digested with the restriction endonucleases HindIII and Xho I and cloned into a vector, i.e. pcDNA3.1/Zeo (Invitrogen), which had likewise been digested with HindIII and Xho I.

c. Hva7-2

The sequence region from position 95 to position 1597 from SEQ ID NO: 5 was amplified by means of a polymerase chain reaction (PCR). Deoxyoligonucleotides having the sequences GCAAGCGCCGCTATGGCCCCTAT-GTTG SEQ ID NO: 13 and TTGCACGATGATATGC-GGTGCCTCGAGCG SEQ ID NO: 14 were used for this. The Pfu polymerase from Stratagene was used as the DNA polymerase in accordance with the manufacturer's instructions. Following amplification, the generated segment was digested with the restriction endonucleases HindIII and Xho I and cloned into a vector, i.e. pcDNA3.1/Zeo (Invitrogen), which had likewise been digested with HindIII and Xho I.

d. Hva7-1/5HT$_3$ and Hva7-2/5HT$_3$ chimaeras

The region from position 335 to position 1036 from SEQ ID NO: 3 (Hva7-1/5HT$_3$ chimaera) and the region from position 95 to position 763 from SEQ ID NO: 5 (Hva7-2/5HT$_3$ chimaera) was in each case fused to the region from position 778 to position 1521 from the Mus musculus 5-HT$_3$ receptor cDNA (sequence in EMBL database: M774425) using the method of overlap extension (Jespersen et al. 1997). The two fragments were subsequently cloned into the pcDNA3.1/Zeo vector by means of TA cloning (Invitrogen, in accordance with the manufacturer's instructions). Constructs containing the correct orientation of the two fragments in the vector were identified by sequencing using the T7 primer (Invitrogen).

Cell Culture and Gene Transfer

HEK293 cells, which express the $\alpha$ subunit of an L-type Ca channel (Zong et al. 1995, Stetzer et al. 1996), were cultured in Dulbecco's modified Eagle's medium and 10% foetal calf serum at 5% $CO_2$ and from 20° C. to 37° C. FuGENE 6 (Boehringer Mannheim GmbH, Mannheim, Germany) was used for the gene transfer in accordance with the manufacturer's instructions. At from 24 h to 48 h after the gene transfer, the cells were sown at various densities in microtitre plates. Recombinantly altered cells were selected by growth in Dulbecco's modified Eagle's medium and 10% foetal calf serum and 150–500 µg/ml of Zeocin/ml over a period of from 3 to 4 weeks. Individual resistant clones were analyzed as described below.

Fura-2 Measurements

The alterations in the intracellular calcium concentration were measured using Fura-2. A stock solution containing 2 mM Fura-2-acetoxy methyl ester (Sigma) in dimethyl sulphoxide (DMSO) was diluted to a final concentration of 5–10 µM in serum-free minimal essential medium (MEM, Gibco) containing 1% bovine serum albumin and 5 mM calcium chloride. The cells were incubated for from 45 to 60 min in this solution in a microtitre plate. The cells were then washed twice in Tyrode solution buffered with N-(2-hydroxyethyl)piperazine-N'-(2-ethanesulphonic acid) (5 mM HEPES) (HEPES-buffered salt solution containing 130 mM NaCl, 5 mM KCl, 2 mM $CaCl_2$, 1 mM $MgCl_2$, 5 mM $NaHCO_3$, 10 mM glucose). 100 µl Tyrode buffer were added to the wells of the microtitre plate and the cells were illuminated alternately, under a fluorescence microscope (Nikon Diaphot), with light of 340 nm and 380 nm wavelength. A series of video images (exposure time per image 100 ms) were taken with pauses of 3 seconds and stored, as digitalized images, in an image analysis computer (Leica, Quantimet 570). After 8 images had been taken (measurement point 4.0 in FIG. 1), nicotine was added to a final concentration of 500 μM and the measurement series was continued. The fluorescence intensity of the cells when illuminating with light of 380 nm wavelength was divided by the corresponding intensity at 340 nm and in this way a ratio was formed which represents the relative increase in calcium concentration (Grynkiewicz et al. 1985).

PRIOR ART

Bossy et al. (1988) Conservation of neural nicotinic acetylcholine receptors from Drosophila to vertebrate central nervous systems, EMBO J. 7, 611–618

Breer et al. (1987) Molecular properties and functions of insect acetylcholine receptors, J. Insect Physiol. 33, 771–790

Buckingham et al. (1997) Imidacloprid actions on insect neuronal acetylcholine receptors, J.Exp. Biol. 200, 2685–2692

Changeux et al. (1992) The functional architecture of the nicotinic acetylcholine receptor explored by affinity labelling and site-directed mutagenesis, Quarterly Review of Biophysics 25, 395–432

Claudio et al. (1983) Nucleotide and deduced amino acid sequences of Torpedo californica acetylcholine receptor g subunit, Proc. Natl. Acad. Sci. USA 80, 1111–1115

Devereux et al. (1984), Nucleic Acids Research 12, 387

Devillers-Thiery et al. (1983) Complete mRNA coding sequence of the acetylcholine binding α-subunit of Torpedo marmorata acetylcholine receptor: a model for the transmembrane organization of the polypeptide chain, Proc. Natl. Acad. Sci. USA 80, 2067–2071

Elgoyhen et al. (1997) U.S. Pat. No. 5,683,912

Eastham et al. (1998) Characterisation of a nicotinic acetylcholine receptor from the insect Manduca sexta, Eur. J. Neurosci 10, 879–889

Grynkiewicz et al. (1985) A new generation of Ca2+ indicators with greatly improved fluorescence properties, J. Biol. Chem. 260, 3440–3450

Hay et al. (1997), P element insertion-dependent gene activation in the Drosophila eye, Proceedings of The National Academy of Sciences of The United States of America 94 (10), 5195–5200

Hermans-Borgmeyer et al. (1986) Primary structure of a developmentally regulated nicotinic acetylcholine receptor protein from Drosophila EMBO J. 5, 1503–1508

Heinemann et al. (1997) U.S. Pat. No 5,591,590

Jespersen et al. (1997) Efficient Non-PCR-Mediated Overlap Extension of PCR Fragments by Exonuclease "End Polishing", Biotechniques, 23, 48–52

Lindstrom et al. (1997) U.S. Pat. No. 5,599,709

Marshall et al. (1990) Sequence and functional expression of a single α subunit of an insect nicotinic acetylcholine receptor, EMBO J. 9, 4391–4398

Noda et al. (1982), Primary structure of α-subunit precursor of Torpedo californica acetylcholine receptor deduced from cDNA sequence, Nature 299, 793–797

Noda et al. (1983a), Primary structures of β- and δ-subunit precursor of Torpedo californica acetylcholine receptor deduced from cDNA sequences, Nature 301, 251–255

Noda et al. (1983b), Structural homology of Torpedo californica acetylcholine receptor subunits, Nature 302, 528–532

Ortells et al. (1995), Evolutionary history of the ligand-gated ion-channel super-family of receptors, Trends in Neurosience 18, 121–127

Plasterk (1996), The Tc1/mariner transposon family, Transposable Elements, Current Topics in Microbiology and Immunology 204, 125–143

Sambrook et al. (1989), Molecular Cloning, A Laboratory Manual, 2nd ed. Cold Spring Harbour Press Sawruk et al. (1990a), EMBO J. 9, 2671–2677 Heterogeneity of Drosophila nicotinic acetylcholine receptors: SAD, a novel developmentally regulated α-subunit Sawruk et al. (1990b), SBD, a novel structural subunit of the Drosophila nicotinic acetylcholine receptor, shares its genomic localization with two a-subunits, FEBS Lett. 273, 177–181

Schloβ et al. (1988), Neuronal acetylcholine receptors of Drosophila: the ARD protein is a component of a high-affinity α-bungarotoxin binding complex, EMBO J. 7, 2889–2984

Stetzer et al. (1996) Stable expression in HEK-293 cells of the rat α3/β4 subtype of neuronal nicotinic acetylcholine receptor, FEBS Lett. 397, 39–44

Zong et al. (1995) On the regulation of the expressed L-type calcium channel by cAMP-dependent phosphorylation, Pflügers Arch.—Eur. J. Physiol. 430, 340–347.

What is claimed is:

1. An isolated nucleic acid comprising a sequence selected from
   (a) a sequence comprising nucleotide No. 372 to nucleotide No. 2681 of SEQ ID NO: 1, nucleotide No. 335 to nucleotide No. 1822 of SEQ ID NO: 3 or nucleotide No. 95 to nucleotide No. 1597 of SEQ ID NO: 5,
   (b) a sequence complementary to the entire length of one of the sequences defined under (a), and
   (c) a sequence which, due to degeneracy of the genetic code, encodes the same amino acid sequences as those encoded by the sequences defined under (a),
   wherein nucleotides 372–2681 of SEQ ID NO:1, nucleotides 335–1822 of SEQ ID NO:3, and nucleotides 95–1597 of SEQ ID NO: 5 each encode an acetylcholine receptor subunit having the ability to form homooligomeric acetylcholine receptors when expressed in a host cell.

2. A vector which comprises at least one nucleic acid of claim 1.

3. The vector of claim 2, wherein the at least one nucleic acid is functionally linked to regulatory sequences which ensure expression of the at least one nucleic acid in a prokaryotic cell or a eukaryotic cell.

4. A host cell which contains the nucleic acid of claim 1.

5. The host cell of claim 4, wherein said host cell is a prokaryotic cell or a eukaryotic cell.

6. The host cell of claim 5, wherein the prokaryotic cell is *E.coli*.

7. The host cell of claim 5, wherein the eukaryotic cell is a mammalian cell or an insect cell.

8. A process for preparing a polypeptide encoded by a nucleic acid of claim 1 comprising
   (a) culturing a prokaryotic cell or a eukaryotic cell in a culture medium, said prokaryotic cell or said eukaryotic cell comprising a vector comprising at least one nucleic acid of claim 1, wherein the at least one nucleic acid is functionally linked to regulatory sequences which ensure expression of the at least one nucleic acid in the prokaryotic cell or the eukaryotic cell and wherein culture conditions allow expression of the polypeptide or polypeptides encoded by the at least one nucleic acid, and
   (b) isolating the encoded polypeptide or polypeptides from the prokaryotic cell or the eukaryotic cell and/or optionally where the encoded polypeptide or polypeptides are secreted in the culture medium, isolating the polypeptide or polypeptides from the culture medium.

9. A host cell containing the vector according to claim 2.

10. A host cell containing the vector according to claim 3.

11. The host cell of claim 9 wherein said host cell is a prokaryotic cell or a eukaryotic cell.

12. The host cell of claim 10 wherein said host cell is a prokaryotic cell or a eukaryotic cell.

13. The host cell of claim 11 wherein said host cell is an *E. coli* cell.

14. The host cell of claim 12 wherein said host cell is an *E. coli* cell.

15. The host cell of claim 11 wherein said host cell is a mammalian cell or an insect cell.

16. The host cell of claim 12 wherein said host cell is a mammalian cell or an insect cell.

* * * * *

SEQUENCE LISTING

<160> NUMBER OF SEQ ID NOS: 14

<210> SEQ ID NO 1
<211> LENGTH: 2886
<212> TYPE: DNA
<213> ORGANISM: Drosophila melanogaster
<220> FEATURE:
<221> NAME/KEY: CDS
<222> LOCATION: (372)..(2681)

<400> SEQUENCE: 1

```
ggcacgagaa aaagttgtgg tataaacttt tattgtagga aaacgcataa aaataataga      60
aaaacgctct tcgggttgta aagaaaataa gaagacaaaa gaaagacatg aaaacgttgc     120
aaacaataaa gcatatactt gccatattga tataaaggga aatcgtgaaa aggcggtgaa     180
```

|  |  |
|---|---|
| aatttcgtaa gattagttgg tattaagggc agcccatgca cacagctaaa aagggaacta | 240 |
| aaaaaacccc gcacagaaca atgaaagctg cagcagctgg ataaggccga caaaaccgaa | 300 |
| aattatatta ttgtaatcta gtagagagca gacaacatat ccgctggcaa caaccaacac | 360 |

| | |
|---|---|
| cgaaagagac t atg aaa aat gca caa ctg aaa ctg act gaa gtt gac gat<br>              Met Lys Asn Ala Gln Leu Lys Leu Thr Glu Val Asp Asp<br>               1              5                  10 | 410 |
| gat gag ctg tgg ctg gca gta aga tta gcg cac tgc agc agc aac ttt<br>Asp Glu Leu Trp Leu Ala Val Arg Leu Ala His Cys Ser Ser Asn Phe<br>       15                  20                25 | 458 |
| agc agc agt agc agc aca aga acc acc agc agc aac cag agg cac aac<br>Ser Ser Ser Ser Ser Thr Arg Thr Thr Ser Ser Asn Gln Arg His Asn<br> 30                35              40              45 | 506 |
| cag caa ctc aca aca ctg caa cca agg agc tta agt aca aaa cac cac<br>Gln Gln Leu Thr Thr Leu Gln Pro Arg Ser Leu Ser Thr Lys His His<br>            50              55              60 | 554 |
| agc aac att gca agc gag cag cac aat agc cag caa cag gag cca gca<br>Ser Asn Ile Ala Ser Glu Gln His Asn Ser Gln Gln Gln Glu Pro Ala<br>       65                  70                75 | 602 |
| tcg aag gac gag gat gta gcc aac cac ggt aga agc aat gac cag cag<br>Ser Lys Asp Glu Asp Val Ala Asn His Gly Arg Ser Asn Asp Gln Gln<br>          80                85              90 | 650 |
| acg cat ctg caa cag cta gac agc agc aac atg ttg tcg cca aag aca<br>Thr His Leu Gln Gln Leu Asp Ser Ser Asn Met Leu Ser Pro Lys Thr<br> 95                100             105 | 698 |
| gcc gca gca gca act gct gcc ggc gat gaa gca aca acc caa caa cca<br>Ala Ala Ala Ala Thr Ala Ala Gly Asp Glu Ala Thr Thr Gln Gln Pro<br>110               115               120             125 | 746 |
| aca aac ata aga ctg tgt gca cgc aag cga caa cga ttg cgt cgc cga<br>Thr Asn Ile Arg Leu Cys Ala Arg Lys Arg Gln Arg Leu Arg Arg Arg<br>            130             135              140 | 794 |
| cga aaa aga aaa cca gca acc cca aac gaa aca gat atc aag aaa caa<br>Arg Lys Arg Lys Pro Ala Thr Pro Asn Glu Thr Asp Ile Lys Lys Gln<br>           145              150            155 | 842 |
| cag caa ctt agc atg cct ccc ttc aaa acg cgc aaa tcc acg gac acc<br>Gln Gln Leu Ser Met Pro Pro Phe Lys Thr Arg Lys Ser Thr Asp Thr<br>        160             165              170 | 890 |
| tac agc aca cca gca gca aca acc agc tgt ccg aca gcc acc tac atg<br>Tyr Ser Thr Pro Ala Ala Thr Thr Ser Cys Pro Thr Ala Thr Tyr Met<br>175               180               185 | 938 |
| caa tgt cga gcc agc gac aat gag ttc agt att ccg ata tcg aga cat<br>Gln Cys Arg Ala Ser Asp Asn Glu Phe Ser Ile Pro Ile Ser Arg His<br>190               195              200             205 | 986 |
| gat aga gta tcc acg gcc aca ttc gcc tgg gtg ttg cat gtg ctg cag<br>Asp Arg Val Ser Thr Ala Thr Phe Ala Trp Val Leu His Val Leu Gln<br>           210              215              220 | 1034 |
| gtg ctg ctc gtg tcg ctg caa cag tgg caa ctt cac gtg caa cag cga<br>Val Leu Leu Val Ser Leu Gln Gln Trp Gln Leu His Val Gln Gln Arg<br>             225              230             235 | 1082 |
| tcg gtg cta ctg ttc aga agg atc gca gcg agc acc atc gcc ttc att<br>Ser Val Leu Leu Phe Arg Arg Ile Ala Ala Ser Thr Ile Ala Phe Ile<br>        240             245              250 | 1130 |
| tcc tat tta ggc agc ttt gca gcg caa ctg aaa aat agc agc agc agc<br>Ser Tyr Leu Gly Ser Phe Ala Ala Gln Leu Lys Asn Ser Ser Ser Ser<br>255               260               265 | 1178 |
| agt agc agc agc aac agc agc aac aac agc agc acg caa ata tta aac<br>Ser Ser Ser Ser Asn Ser Ser Asn Asn Ser Ser Thr Gln Ile Leu Asn<br>270               275              280             285 | 1226 |
| gga ctt aat aaa cac tca tgg ata ttt tta ttg ata tat ttg aat tta | 1274 |

```
                Gly Leu Asn Lys His Ser Trp Ile Phe Leu Leu Ile Tyr Leu Asn Leu
                            290                 295                 300 tct gct aaa gtt tgc cta gca gga tat cat gaa aag aga ctg tta cac          1322
Ser Ala Lys Val Cys Leu Ala Gly Tyr His Glu Lys Arg Leu Leu His
            305                 310                 315 gat ctt ttg gat cct tat aat aca cta gaa cgt ccc gtt ctc aat gaa          1370
Asp Leu Leu Asp Pro Tyr Asn Thr Leu Glu Arg Pro Val Leu Asn Glu
        320                 325                 330 tcg gac ccg tta caa tta agc ttt ggt tta act tta atg caa att atc          1418
Ser Asp Pro Leu Gln Leu Ser Phe Gly Leu Thr Leu Met Gln Ile Ile
    335                 340                 345 gat gtg gac gag aaa aat caa ttg cta gtc act aat gtg tgg tta aaa          1466
Asp Val Asp Glu Lys Asn Gln Leu Leu Val Thr Asn Val Trp Leu Lys
350                 355                 360                 365 ctg gag tgg aac gac atg aat ctc cgc tgg aac acc tcc gac tat ggc          1514
Leu Glu Trp Asn Asp Met Asn Leu Arg Trp Asn Thr Ser Asp Tyr Gly
                370                 375                 380 gga gtt aag gat ctg cga ata ccg ccg cat cgc atc tgg aag ccg gac          1562
Gly Val Lys Asp Leu Arg Ile Pro Pro His Arg Ile Trp Lys Pro Asp
            385                 390                 395 gtg ctg atg tac aac agt gcg gat gag gga ttt gac ggc acc tac cag          1610
Val Leu Met Tyr Asn Ser Ala Asp Glu Gly Phe Asp Gly Thr Tyr Gln
        400                 405                 410 acg aac gtg gtg gtg cgg aac aac ggc tcg tgt cta tac gtt ccg ccg          1658
Thr Asn Val Val Val Arg Asn Asn Gly Ser Cys Leu Tyr Val Pro Pro
    415                 420                 425 ggg atc ttc aag tcg acg tgc aag atc gac atc acg tgg ttc ccc ttc          1706
Gly Ile Phe Lys Ser Thr Cys Lys Ile Asp Ile Thr Trp Phe Pro Phe
430                 435                 440                 445 gat gac cag cgg tgc gag atg aag ttc ggc agt tgg acc tac gac gga          1754
Asp Asp Gln Arg Cys Glu Met Lys Phe Gly Ser Trp Thr Tyr Asp Gly
                450                 455                 460 ttc cag ctg gat tta caa tta caa gat gaa act ggc ggt gat atc agc          1802
Phe Gln Leu Asp Leu Gln Leu Gln Asp Glu Thr Gly Gly Asp Ile Ser
            465                 470                 475 agt tac gtg ctc aac ggc gag tgg gaa cta ctg ggt gtg ccc ggc aaa          1850
Ser Tyr Val Leu Asn Gly Glu Trp Glu Leu Leu Gly Val Pro Gly Lys
        480                 485                 490 cgt aac gag atc tat tac aac tgc tgc ccg gaa ccc tat ata gac atc          1898
Arg Asn Glu Ile Tyr Tyr Asn Cys Cys Pro Glu Pro Tyr Ile Asp Ile
    495                 500                 505 acc ttc gcc atc atc atc cgc cga cga aca ctg tac tat ttc ttc aac          1946
Thr Phe Ala Ile Ile Ile Arg Arg Arg Thr Leu Tyr Tyr Phe Phe Asn
510                 515                 520                 525 ctg atc ata cct tgt gta ctg att gcc tcc atg gcc ttg ctc gga ttc          1994
Leu Ile Ile Pro Cys Val Leu Ile Ala Ser Met Ala Leu Leu Gly Phe
                530                 535                 540 acc ctg ccg cca gat tcg ggt gaa aaa tta tcg ctg ggt gtt acc atc          2042
Thr Leu Pro Pro Asp Ser Gly Glu Lys Leu Ser Leu Gly Val Thr Ile
            545                 550                 555 ttg ctc tcg ctg acc gtg ttt ctg aat atg gtt gcc gag aca atg ccg          2090
Leu Leu Ser Leu Thr Val Phe Leu Asn Met Val Ala Glu Thr Met Pro
        560                 565                 570 gct act tcc gat gcg gtg cca ttg tgg ata cgc atc gtg ttt ttg tgc          2138
Ala Thr Ser Asp Ala Val Pro Leu Trp Ile Arg Ile Val Phe Leu Cys
    575                 580                 585 tgg ctg cca tgg ata ttg cga atg agt cgc cca gga cga ccg ctg atc          2186
Trp Leu Pro Trp Ile Leu Arg Met Ser Arg Pro Gly Arg Pro Leu Ile
590                 595                 600                 605
```

-continued

| | | | | |
|---|---|---|---|---|
| cta gag ttc ccg acc acg ccc tgt tcg gac aca tcc tcc gag cgg aag<br>Leu Glu Phe Pro Thr Thr Pro Cys Ser Asp Thr Ser Ser Glu Arg Lys<br>610                    615                  620 | 2234 |

```
cta gag ttc ccg acc acg ccc tgt tcg gac aca tcc tcc gag cgg aag     2234
Leu Glu Phe Pro Thr Thr Pro Cys Ser Asp Thr Ser Ser Glu Arg Lys
            610                 615                 620 cac cag ata ctc tcc gac gtt gag ctg aaa gag cgc tcg tcg aaa tcg     2282
His Gln Ile Leu Ser Asp Val Glu Leu Lys Glu Arg Ser Ser Lys Ser
                625                 630                 635 ctg ctg gcc aac gta cta gac atc gat gat gac ttc cgg cac aat tgt     2330
Leu Leu Ala Asn Val Leu Asp Ile Asp Asp Asp Phe Arg His Asn Cys
        640                 645                 650 cgc ccc atg acg ccc ggc gga aca ctg cca cac aac ccg gct ttc tat     2378
Arg Pro Met Thr Pro Gly Gly Thr Leu Pro His Asn Pro Ala Phe Tyr
    655                 660                 665 cgc acg gtt tat gga caa ggc gac gat ggc agc att ggg cca att ggc     2426
Arg Thr Val Tyr Gly Gln Gly Asp Asp Gly Ser Ile Gly Pro Ile Gly
670                 675                 680                 685 agc acc cga atg ccg gat gcg gtc acc cat cat acg tgc atc aaa tca     2474
Ser Thr Arg Met Pro Asp Ala Val Thr His His Thr Cys Ile Lys Ser
                690                 695                 700 tca act gaa tat gaa tta ggt tta atc tta aag gaa att cgc ttt ata     2522
Ser Thr Glu Tyr Glu Leu Gly Leu Ile Leu Lys Glu Ile Arg Phe Ile
            705                 710                 715 act gat cag cta cgt aaa gat gac gag tgc aat gac att gcc aat gat     2570
Thr Asp Gln Leu Arg Lys Asp Asp Glu Cys Asn Asp Ile Ala Asn Asp
        720                 725                 730 tgg aaa ttt gca gct atg gtc gtt gac aga ctg tgc ctt atc ata ttc     2618
Trp Lys Phe Ala Ala Met Val Val Asp Arg Leu Cys Leu Ile Ile Phe
    735                 740                 745 aca atg ttc gca ata tta gcc aca ata gct gta cta cta tcg gca cca     2666
Thr Met Phe Ala Ile Leu Ala Thr Ile Ala Val Leu Leu Ser Ala Pro
750                 755                 760                 765 cat att att gtc tcg tagccatatg ggcgaggtgg ttattgttat tggttttatt     2721
His Ile Ile Val Ser
                770 ataaaatcaa tttgttaatt attaaattaa taacgaaact ctttaagtaa attaaaacta    2781 aaaagacact aaaaaagcac aaaaaaatag gaaaatacat gataaaaccc atgaactaaa    2841 taatacatcc aagaaaaacc aaaacaaaaa aaaaaaaaaa aaaaa                    2886
```

<210> SEQ ID NO 2
<211> LENGTH: 770
<212> TYPE: PRT
<213> ORGANISM: Drosophila melanogaster
<400> SEQUENCE: 2

```
Met Lys Asn Ala Gln Leu Lys Leu Thr Glu Val Asp Asp Asp Glu Leu
 1               5                  10                  15

Trp Leu Ala Val Arg Leu Ala His Cys Ser Ser Asn Phe Ser Ser Ser
            20                  25                  30

Ser Ser Thr Arg Thr Thr Ser Ser Asn Gln Arg His Asn Gln Gln Leu
        35                  40                  45

Thr Thr Leu Gln Pro Arg Ser Leu Ser Thr Lys His His Ser Asn Ile
    50                  55                  60

Ala Ser Glu Gln His Asn Ser Gln Gln Gln Glu Pro Ala Ser Lys Asp
65                  70                  75                  80

Glu Asp Val Ala Asn His Gly Arg Ser Asn Asp Gln Gln Thr His Leu
                85                  90                  95

Gln Gln Leu Asp Ser Ser Asn Met Leu Ser Pro Lys Thr Ala Ala Ala
           100                 105                 110
```

-continued

Ala Thr Ala Ala Gly Asp Glu Ala Thr Thr Gln Gln Pro Thr Asn Ile
                115                 120                 125

Arg Leu Cys Ala Arg Lys Arg Gln Arg Leu Arg Arg Arg Lys Arg
    130                 135                 140

Lys Pro Ala Thr Pro Asn Glu Thr Asp Ile Lys Lys Gln Gln Gln Leu
145                 150                 155                 160

Ser Met Pro Pro Phe Lys Thr Arg Lys Ser Thr Asp Thr Tyr Ser Thr
                165                 170                 175

Pro Ala Ala Thr Thr Ser Cys Pro Thr Ala Thr Tyr Met Gln Cys Arg
                180                 185                 190

Ala Ser Asp Asn Glu Phe Ser Ile Pro Ile Ser Arg His Asp Arg Val
            195                 200                 205

Ser Thr Ala Thr Phe Ala Trp Val Leu His Val Leu Gln Val Leu Leu
    210                 215                 220

Val Ser Leu Gln Gln Trp Gln Leu His Val Gln Gln Arg Ser Val Leu
225                 230                 235                 240

Leu Phe Arg Arg Ile Ala Ala Ser Thr Ile Ala Phe Ile Ser Tyr Leu
                245                 250                 255

Gly Ser Phe Ala Ala Gln Leu Lys Asn Ser Ser Ser Ser Ser Ser
                260                 265                 270

Ser Asn Ser Ser Asn Asn Ser Ser Thr Gln Ile Leu Asn Gly Leu Asn
    275                 280                 285

Lys His Ser Trp Ile Phe Leu Leu Ile Tyr Leu Asn Leu Ser Ala Lys
            290                 295                 300

Val Cys Leu Ala Gly Tyr His Glu Lys Arg Leu Leu His Asp Leu Leu
305                 310                 315                 320

Asp Pro Tyr Asn Thr Leu Glu Arg Pro Val Leu Asn Glu Ser Asp Pro
                325                 330                 335

Leu Gln Leu Ser Phe Gly Leu Thr Leu Met Gln Ile Ile Asp Val Asp
                340                 345                 350

Glu Lys Asn Gln Leu Leu Val Thr Asn Val Trp Leu Lys Leu Glu Trp
            355                 360                 365

Asn Asp Met Asn Leu Arg Trp Asn Thr Ser Asp Tyr Gly Gly Val Lys
            370                 375                 380

Asp Leu Arg Ile Pro Pro His Arg Ile Trp Lys Pro Asp Val Leu Met
385                 390                 395                 400

Tyr Asn Ser Ala Asp Glu Gly Phe Asp Gly Thr Tyr Gln Thr Asn Val
                405                 410                 415

Val Val Arg Asn Asn Gly Ser Cys Leu Tyr Val Pro Pro Gly Ile Phe
            420                 425                 430

Lys Ser Thr Cys Lys Ile Asp Ile Thr Trp Phe Pro Phe Asp Gln
    435                 440                 445

Arg Cys Glu Met Lys Phe Gly Ser Trp Thr Tyr Asp Gly Phe Gln Leu
    450                 455                 460

Asp Leu Gln Leu Gln Asp Glu Thr Gly Gly Asp Ile Ser Ser Tyr Val
465                 470                 475                 480

Leu Asn Gly Glu Trp Glu Leu Leu Gly Val Pro Gly Lys Arg Asn Glu
                485                 490                 495

Ile Tyr Tyr Asn Cys Cys Pro Glu Pro Tyr Ile Asp Ile Thr Phe Ala
            500                 505                 510

Ile Ile Ile Arg Arg Arg Thr Leu Tyr Tyr Phe Phe Asn Leu Ile Ile
        515                 520                 525

Pro Cys Val Leu Ile Ala Ser Met Ala Leu Leu Gly Phe Thr Leu Pro

```
                    530                  535                  540
Pro Asp Ser Gly Glu Lys Leu Ser Leu Gly Val Thr Ile Leu Leu Ser
545                 550                  555                 560

Leu Thr Val Phe Leu Asn Met Val Ala Glu Thr Met Pro Ala Thr Ser
                565                  570                 575

Asp Ala Val Pro Leu Trp Ile Arg Ile Val Phe Leu Cys Trp Leu Pro
            580                  585                 590

Trp Ile Leu Arg Met Ser Arg Pro Gly Arg Pro Leu Ile Leu Glu Phe
        595                  600                 605

Pro Thr Thr Pro Cys Ser Asp Thr Ser Glu Arg Lys His Gln Ile
    610                  615                 620

Leu Ser Asp Val Glu Leu Lys Glu Arg Ser Ser Lys Ser Leu Leu Ala
625                 630                  635                 640

Asn Val Leu Asp Ile Asp Asp Phe Arg His Asn Cys Arg Pro Met
                645                  650                 655

Thr Pro Gly Gly Thr Leu Pro His Asn Pro Ala Phe Tyr Arg Thr Val
            660                  665                 670

Tyr Gly Gln Gly Asp Asp Gly Ser Ile Gly Pro Ile Gly Ser Thr Arg
        675                  680                 685

Met Pro Asp Ala Val Thr His His Thr Cys Ile Lys Ser Ser Thr Glu
    690                  695                 700

Tyr Glu Leu Gly Leu Ile Leu Lys Glu Ile Arg Phe Ile Thr Asp Gln
705                 710                  715                 720

Leu Arg Lys Asp Asp Glu Cys Asn Asp Ile Ala Asn Asp Trp Lys Phe
                725                  730                 735

Ala Ala Met Val Val Asp Arg Leu Cys Leu Ile Ile Phe Thr Met Phe
            740                  745                 750

Ala Ile Leu Ala Thr Ile Ala Val Leu Leu Ser Ala Pro His Ile Ile
        755                  760                 765

Val Ser
    770

<210> SEQ ID NO 3
<211> LENGTH: 3700
<212> TYPE: DNA
<213> ORGANISM: Heliothis virescens
<220> FEATURE:
<221> NAME/KEY: CDS
<222> LOCATION: (335)..(1822)

<400> SEQUENCE: 3
ggcacgagcc gctgccccac ggtcggccgc actccgctga acaacaatgc tcaaaaacac      60
gccgtgactc cacacacatc ccctcggcgc agtaggcgat gtttgaggat cggacggcac     120
gcgtggccgt cggcgagcgg tcgtgaacaa gttgcataca tatgaaaacc gtaaaaagat     180
tgaattttaa gccgatcgtg ttcgatagat cctaatagag aagcgggagt gcggcgtttg     240
gtaggcgggg gtcgagtcgc gcggtcgggg gaaatggcgc ggcgcggggc ggcggcggcg     300
gcggcgcgcg gcgcggcggc gtcgcggcgc tgac atg ggc ggg cgg gcg cgc cgc     355
                                    Met Gly Gly Arg Ala Arg Arg
                                      1               5 tcg cac ttg gcg gcg ccc gcg ggc ctg ctg ctg ctg tgc ctg ctc             403
Ser His Leu Ala Ala Pro Ala Gly Leu Leu Leu Leu Cys Leu Leu
            10                  15                  20 tgg ccg agg ggg gca cgc tgc ggg tac cac gag aag cgg cta ctg cac         451
Trp Pro Arg Gly Ala Arg Cys Gly Tyr His Glu Lys Arg Leu Leu His
        25                  30                  35
```

```
cac cta ttg gac cac tac aac gta ctg gag agg ccc gtc gtc aac gag    499
His Leu Leu Asp His Tyr Asn Val Leu Glu Arg Pro Val Val Asn Glu
 40              45                  50                  55 agc gac ccg ctg cag ctc tcc ttc ggc ctc acg ctc atg cag atc atc    547
Ser Asp Pro Leu Gln Leu Ser Phe Gly Leu Thr Leu Met Gln Ile Ile
             60                  65                  70 gac gtg gac gag aag aac cag ctt tta ata aca aac atc tgg cta aaa    595
Asp Val Asp Glu Lys Asn Gln Leu Leu Ile Thr Asn Ile Trp Leu Lys
                 75                  80                  85 cta gag tgg aat gat atg aac ttg agg tgg aac act tca gat ttc ggc    643
Leu Glu Trp Asn Asp Met Asn Leu Arg Trp Asn Thr Ser Asp Phe Gly
         90                  95                 100 ggg gtc aaa gat tta aga gtg cca ccc cac aga cta tgg aaa cca gac    691
Gly Val Lys Asp Leu Arg Val Pro Pro His Arg Leu Trp Lys Pro Asp
    105                 110                 115 gtc ctt atg tac aac agc gcg gac gaa ggg ttc gac agc acg tat cca    739
Val Leu Met Tyr Asn Ser Ala Asp Glu Gly Phe Asp Ser Thr Tyr Pro
120                 125                 130                 135 acg aac gtg gtg gtg cgg aac aac ggc tcg tgt ctg tac gtc ccg ccc    787
Thr Asn Val Val Val Arg Asn Asn Gly Ser Cys Leu Tyr Val Pro Pro
                140                 145                 150 ggc atc ttc aag agc acc tgc aag atc gac atc acc tgg ttc ccc ttc    835
Gly Ile Phe Lys Ser Thr Cys Lys Ile Asp Ile Thr Trp Phe Pro Phe
            155                 160                 165 gac gac caa cga tgc gag atg aag ttt ggc agc tgg act tat gat ggt    883
Asp Asp Gln Arg Cys Glu Met Lys Phe Gly Ser Trp Thr Tyr Asp Gly
        170                 175                 180 tat cag ttg gat cta caa cta cag gat gaa ggg ggc gga gat ata agc    931
Tyr Gln Leu Asp Leu Gln Leu Gln Asp Glu Gly Gly Gly Asp Ile Ser
    185                 190                 195 agt ttt gtc acg aat ggc gaa tgg gag tta ata gga gtc ccc ggc aag    979
Ser Phe Val Thr Asn Gly Glu Trp Glu Leu Ile Gly Val Pro Gly Lys
200                 205                 210                 215 cgc aac gag atc tac tac aac tgt tgt ccg gag cca tac atc gac atc   1027
Arg Asn Glu Ile Tyr Tyr Asn Cys Cys Pro Glu Pro Tyr Ile Asp Ile
                220                 225                 230 acg ttt gcg gtg gtg atc cgg agg aaa acg ctc tac tac ttc ttc aat   1075
Thr Phe Ala Val Val Ile Arg Arg Lys Thr Leu Tyr Tyr Phe Phe Asn
            235                 240                 245 ctg atc gtg ccc tgc gtg ctc atc gcc tcc atg gct cta ttg ggg ttc   1123
Leu Ile Val Pro Cys Val Leu Ile Ala Ser Met Ala Leu Leu Gly Phe
        250                 255                 260 acc ttg cct cca gac tcc gga gaa aag ttg tct tta ggt gtg acg ata   1171
Thr Leu Pro Pro Asp Ser Gly Glu Lys Leu Ser Leu Gly Val Thr Ile
    265                 270                 275 tta ctg tcg ttg acg gtg ttc ctc aac atg gtg gcg gag acg atg cca   1219
Leu Leu Ser Leu Thr Val Phe Leu Asn Met Val Ala Glu Thr Met Pro
280                 285                 290                 295 gcg acg tcg gac gcc gtg ccc ttg ctc ggc acc tac ttc aac tgc atc   1267
Ala Thr Ser Asp Ala Val Pro Leu Leu Gly Thr Tyr Phe Asn Cys Ile
                300                 305                 310 atg ttc atg gtg gct tcc tcc gtc gtc tcc acc ata ctg atc ctc aac   1315
Met Phe Met Val Ala Ser Ser Val Val Ser Thr Ile Leu Ile Leu Asn
            315                 320                 325 tac cac cac cgg cac gca gac act cac gaa atg agt gat tgg att cgt   1363
Tyr His His Arg His Ala Asp Thr His Glu Met Ser Asp Trp Ile Arg
        330                 335                 340 tgc gtg ttc ctt tat tgg ctg ccg tgg gtg ctg cgc atg tca cgg ccc   1411
Cys Val Phe Leu Tyr Trp Leu Pro Trp Val Leu Arg Met Ser Arg Pro
```

-continued

|  |  |  |  |  |  |  |  |  |  |  |  |  |  |  |  |
|---|---|---|---|---|---|---|---|---|---|---|---|---|---|---|---|
|  | 345 |  |  |  | 350 |  |  |  |  | 355 |  |  |  |  |  |
| ggc | tcg | gcg | acg | acg | ccg | ccg | ccg | gcg | cgc | gta | cct | ccg | ccg | ccg | gac | 1459 |
| Gly | Ser | Ala | Thr | Thr | Pro | Pro | Pro | Ala | Arg | Val | Pro | Pro | Pro | Pro | Asp |
|  | 360 |  |  |  |  | 365 |  |  |  |  | 370 |  |  |  |  | 375 |
| ctg | gag | ctg | cgc | gag | cgc | tcc | tcc | aag | tcg | ctc | cta | gcg | aac | gtg | ctc | 1507 |
| Leu | Glu | Leu | Arg | Glu | Arg | Ser | Ser | Lys | Ser | Leu | Leu | Ala | Asn | Val | Leu |
|  |  |  |  | 380 |  |  |  |  | 385 |  |  |  |  | 390 |  |
| gac | atc | gat | gac | gac | ttc | cgc | cac | ccg | caa | gcg | cag | cag | ccg | caa | tgc | 1555 |
| Asp | Ile | Asp | Asp | Asp | Phe | Arg | His | Pro | Gln | Ala | Gln | Gln | Pro | Gln | Cys |
|  |  |  | 395 |  |  |  |  | 400 |  |  |  |  | 405 |  |  |
| tgc | cga | tac | tac | agg | ggg | ggt | gag | gag | aat | ggc | gcg | ggg | ttg | gcg | gcg | 1603 |
| Cys | Arg | Tyr | Tyr | Arg | Gly | Gly | Glu | Glu | Asn | Gly | Ala | Gly | Leu | Ala | Ala |
|  |  | 410 |  |  |  |  | 415 |  |  |  |  | 420 |  |  |  |
| cac | agt | tgc | ttc | ggt | gtc | gac | tac | gag | ctc | tcc | ctc | att | ctg | aag | gag | 1651 |
| His | Ser | Cys | Phe | Gly | Val | Asp | Tyr | Glu | Leu | Ser | Leu | Ile | Leu | Lys | Glu |
|  | 425 |  |  |  |  | 430 |  |  |  |  | 435 |  |  |  |  |
| att | aga | gtc | atc | aca | gat | cag | atg | cgc | aag | gac | gac | gaa | gat | gcg | gac | 1699 |
| Ile | Arg | Val | Ile | Thr | Asp | Gln | Met | Arg | Lys | Asp | Asp | Glu | Asp | Ala | Asp |
| 440 |  |  |  |  | 445 |  |  |  |  | 450 |  |  |  |  | 455 |
| att | tcg | cgc | gac | tgg | aag | ttc | gcc | gcc | atg | gtc | gtg | gac | aga | ctg | tgc | 1747 |
| Ile | Ser | Arg | Asp | Trp | Lys | Phe | Ala | Ala | Met | Val | Val | Asp | Arg | Leu | Cys |
|  |  |  |  | 460 |  |  |  |  | 465 |  |  |  |  | 470 |  |
| ctt | att | atc | ttt | acc | ctg | ttc | aca | atc | atc | gcc | acg | cta | gcc | gtg | ctg | 1795 |
| Leu | Ile | Ile | Phe | Thr | Leu | Phe | Thr | Ile | Ile | Ala | Thr | Leu | Ala | Val | Leu |
|  |  |  | 475 |  |  |  |  | 480 |  |  |  |  | 485 |  |  |
| ctg | tcc | gcg | cca | cac | atc | atg | gtg | tcg | tagcgacccg | cccgcttgcg |  |  |  |  |  | 1842 |
| Leu | Ser | Ala | Pro | His | Ile | Met | Val | Ser |  |  |  |  |  |  |  |
|  | 490 |  |  |  |  | 495 |  |  |  |  |  |  |  |  |  |

| | |
|---|---|
| gatacgcatg cgaaaagttc tgtgataccg cgaatatttg ttaagttgtg atgagcgaag | 1902 |
| tggcgcggac ggtgacgccg cggcgtcgga gttgccgccg cctgcctcgc cgcccgcgcc | 1962 |
| cccctgtaga cataagttac cgctgactgc caaccctgta cgttcaacaa ataactgccc | 2022 |
| atccgactaa cgtctttat ccccttgaaa aattcagcga ttgtgtaccc ctttcttcca | 2082 |
| agaatacaat gacaaatggt cgtcacgctc agtggaatca atcccgtact cttcgcccga | 2142 |
| tatttcccctt agggtatgtc acgagtttga atgagcggtt ccgtatcaga cgttccgtcc | 2202 |
| ccggaacggt cgtcccctgc gataaagtgg cagtacgtgc tatacaggca cttaaggccg | 2262 |
| ccacgccacg gcgccgcggt gcgctcgggc gcgaacccg cgaccctcac cgctgcaagt | 2322 |
| ggccacccac tagacaagac tgcggcagaa aatatttgca caaaaacgtc ttccttctta | 2382 |
| ccgatgaacg acctgattcg catttaaaat taaactttgt tagaacttct tcgattcttg | 2442 |
| aaatctattg tacagtttag agtttgggcg gtgaaacaat ggccctttgt ttccttcttg | 2502 |
| ttcgattcca tgaatcgtgg ttataatccc tagtttatt ttcggatata tttgtgtcag | 2562 |
| tagctagtat agaactttac aaacaatgtt gattcaattg gtacaggttg tgatatgcct | 2622 |
| cgttgtgaac gggtccgata ttgttataaa tggtaaaata cccatggcta tagcttaata | 2682 |
| aatcgttcgt taaagttgt agttaaacaa atattatttt aataaagtca tatctgggtc | 2742 |
| ttccggaacg acttttacaa ataattaaat tacatattaa tatcacgttt gtacttcttt | 2802 |
| ccatacagtt acagtaattc gtatgctgaa ataatatta gcttgtaaaa ttttcttctt | 2862 |
| cgaaaattta ttcaaacaga tgcgaccatc gtttcaaaca tttacatgta atatagaact | 2922 |
| catttttataa gatatacaac attttataag tacaagaagt tgtaacatga accggttttt | 2982 |
| cgttacatag agggtataac acaaggtgc ctacatattg acagatgcga agcacgatca | 3042 |
| gttgataagc acaggtacac tatatcctga catccgacag tcctgccgct cgtctgccac | 3102 |

-continued

```
actcggaaac attcgacagt tcagtttact gctccgccat catcgattgt taagtttgtt    3162
gttctaactc atcgcattca tttcattcaa aaacattgta aacctctcaa ggggaaaacg    3222
tgttgtaaac agtgagagtg cgcgggtaca accgacacgc gaatgtaccc tcgcaaggct    3282
cctgtaatgt tttcctcttc cgaggtgttg ctgagagtaa tcttagacgg tccgatggaa    3342
gttgcggacc ggatatgatt acaagtcaat gttttttaagt catccgttta tttattgtta   3402
tatcttctta ccattcgcta gaggttgtgt gacgacccgg acggtgggcg ccgcaacccg    3462
cacacgcggg gttccatctt tgtattagat ggaagttgtg cggcatctct ccgtcggcaa    3522
tgggacaacc cgttgtcccc aacatttgtt caattgttag ggttaactct gaattgcact    3582
ttgtttatta aatataaacg aatgaaacaa aaaaaaaaaa aaaaaactcg agagtacttc    3642
tagagcggcc gcgggcccat cgattttcca cccgggtggg gtaccagtaa gtgtaccc     3700
```

<210> SEQ ID NO 4
<211> LENGTH: 496
<212> TYPE: PRT
<213> ORGANISM: Heliothis virescens

<400> SEQUENCE: 4

```
Met Gly Gly Arg Ala Arg Arg Ser His Leu Ala Ala Pro Ala Gly Leu
  1               5                  10                  15

Leu Leu Leu Leu Cys Leu Leu Trp Pro Arg Gly Ala Arg Cys Gly Tyr
                 20                  25                  30

His Glu Lys Arg Leu Leu His His Leu Leu Asp His Tyr Asn Val Leu
             35                  40                  45

Glu Arg Pro Val Val Asn Glu Ser Asp Pro Leu Gln Leu Ser Phe Gly
         50                  55                  60

Leu Thr Leu Met Gln Ile Ile Asp Val Asp Glu Lys Asn Gln Leu Leu
 65                  70                  75                  80

Ile Thr Asn Ile Trp Leu Lys Leu Glu Trp Asn Asp Met Asn Leu Arg
                 85                  90                  95

Trp Asn Thr Ser Asp Phe Gly Gly Val Lys Asp Leu Arg Val Pro Pro
            100                 105                 110

His Arg Leu Trp Lys Pro Asp Val Leu Met Tyr Asn Ser Ala Asp Glu
        115                 120                 125

Gly Phe Asp Ser Thr Tyr Pro Thr Asn Val Val Arg Asn Asn Gly
    130                 135                 140

Ser Cys Leu Tyr Val Pro Pro Gly Ile Phe Lys Ser Thr Cys Lys Ile
145                 150                 155                 160

Asp Ile Thr Trp Phe Pro Phe Asp Asp Gln Arg Cys Glu Met Lys Phe
                165                 170                 175

Gly Ser Trp Thr Tyr Asp Gly Tyr Gln Leu Asp Leu Gln Leu Gln Asp
            180                 185                 190

Glu Gly Gly Gly Asp Ile Ser Ser Phe Val Thr Asn Gly Glu Trp Glu
        195                 200                 205

Leu Ile Gly Val Pro Gly Lys Arg Asn Glu Ile Tyr Tyr Asn Cys Cys
    210                 215                 220

Pro Glu Pro Tyr Ile Asp Ile Thr Phe Ala Val Val Ile Arg Arg Lys
225                 230                 235                 240

Thr Leu Tyr Tyr Phe Phe Asn Leu Ile Val Pro Cys Val Leu Ile Ala
                245                 250                 255

Ser Met Ala Leu Leu Gly Phe Thr Leu Pro Pro Asp Ser Gly Glu Lys
            260                 265                 270
```

```
Leu Ser Leu Gly Val Thr Ile Leu Ser Leu Thr Val Phe Leu Asn
        275                 280                 285

Met Val Ala Glu Thr Met Pro Ala Thr Ser Asp Ala Val Pro Leu Leu
    290                 295                 300

Gly Thr Tyr Phe Asn Cys Ile Met Phe Met Val Ala Ser Ser Val Val
305                 310                 315                 320

Ser Thr Ile Leu Ile Leu Asn Tyr His His Arg His Ala Asp Thr His
                325                 330                 335

Glu Met Ser Asp Trp Ile Arg Cys Val Phe Leu Tyr Trp Leu Pro Trp
        340                 345                 350

Val Leu Arg Met Ser Arg Pro Gly Ser Ala Thr Thr Pro Pro Pro Ala
    355                 360                 365

Arg Val Pro Pro Pro Asp Leu Glu Leu Arg Glu Arg Ser Ser Lys
    370                 375                 380

Ser Leu Leu Ala Asn Val Leu Asp Ile Asp Asp Phe Arg His Pro
385                 390                 395                 400

Gln Ala Gln Gln Pro Gln Cys Cys Arg Tyr Tyr Arg Gly Gly Glu Glu
                405                 410                 415

Asn Gly Ala Gly Leu Ala Ala His Ser Cys Phe Gly Val Asp Tyr Glu
                420                 425                 430

Leu Ser Leu Ile Leu Lys Glu Ile Arg Val Ile Thr Asp Gln Met Arg
                435                 440                 445

Lys Asp Asp Glu Asp Ala Asp Ile Ser Arg Asp Trp Lys Phe Ala Ala
    450                 455                 460

Met Val Val Asp Arg Leu Cys Leu Ile Ile Phe Thr Leu Phe Thr Ile
465                 470                 475                 480

Ile Ala Thr Leu Ala Val Leu Leu Ser Ala Pro His Ile Met Val Ser
                485                 490                 495

<210> SEQ ID NO 5
<211> LENGTH: 3109
<212> TYPE: DNA
<213> ORGANISM: Heliothis virescens
<220> FEATURE:
<221> NAME/KEY: CDS
<222> LOCATION: (95)..(1597)

<400> SEQUENCE: 5
ggcacgagcc ggccgcacgt tgtcccaggc cgcatgagcg cgccggcgtg ctagcgcagc      60
gtgcgcgggt gtggtatgcc cgcgcgtcgc cgct atg gcc cct atg ttg gcg gcc    115
                                    Met Ala Pro Met Leu Ala Ala
                                      1               5 ttg gcg ctg ctg gct ttg ctg ccc gta tcg gag caa ggt cct cac gag      163
Leu Ala Leu Leu Ala Leu Leu Pro Val Ser Glu Gln Gly Pro His Glu
        10                  15                  20 aag aga ctc ctg aac gcg ttg ctg gcg aac tac aac acc ctg gag cga      211
Lys Arg Leu Leu Asn Ala Leu Leu Ala Asn Tyr Asn Thr Leu Glu Arg
    25                  30                  35 ccg gtg gcc aac gag agc gaa ccg cta gag gtc agg ttc ggc ttg acc      259
Pro Val Ala Asn Glu Ser Glu Pro Leu Glu Val Arg Phe Gly Leu Thr
40                  45                  50                  55 ttg cag caa atc att gac gtg gac gag aag aat caa cta ctt ata acc      307
Leu Gln Gln Ile Ile Asp Val Asp Glu Lys Asn Gln Leu Leu Ile Thr
                60                  65                  70 aat ata tgg ctg tcg ttg gag tgg aat gac tac aac ctg agg tgg aac      355
Asn Ile Trp Leu Ser Leu Glu Trp Asn Asp Tyr Asn Leu Arg Trp Asn
            75                  80                  85
```

-continued

```
gac agc gag tat ggc ggg gtc aag gac ctc agg atc acg ccc aac aag      403
Asp Ser Glu Tyr Gly Gly Val Lys Asp Leu Arg Ile Thr Pro Asn Lys
         90                  95                 100 ttg tgg aag ccg gac gtc ctt atg tat aat agt gct gac gag ggt ttt      451
Leu Trp Lys Pro Asp Val Leu Met Tyr Asn Ser Ala Asp Glu Gly Phe
105                 110                 115 gac ggg acc tac cag acc aac gtg gtg gtc aga agc ggc ggt agt tgc      499
Asp Gly Thr Tyr Gln Thr Asn Val Val Val Arg Ser Gly Gly Ser Cys
120                 125                 130                 135 ctg tac gtg cca cct ggc ata ttc aag agc aca tgc aag atg gac atc      547
Leu Tyr Val Pro Pro Gly Ile Phe Lys Ser Thr Cys Lys Met Asp Ile
                140                 145                 150 gcg tgg ttt ccc ttc gac gac caa cac tgt gat atg aag ttc ggt agc      595
Ala Trp Phe Pro Phe Asp Asp Gln His Cys Asp Met Lys Phe Gly Ser
            155                 160                 165 tgg aca tat gac ggc aat cag ttg gat ctg gtg cta aaa gat gag gca      643
Trp Thr Tyr Asp Gly Asn Gln Leu Asp Leu Val Leu Lys Asp Glu Ala
        170                 175                 180 ggc ggc gat cta tcg gac ttc ata aca aat ggg gag tgg tat cta ata      691
Gly Gly Asp Leu Ser Asp Phe Ile Thr Asn Gly Glu Trp Tyr Leu Ile
185                 190                 195 gga atg cca ggc aaa aag aac aca ata aca tac gcg tgc tgc ccc gag      739
Gly Met Pro Gly Lys Lys Asn Thr Ile Thr Tyr Ala Cys Cys Pro Glu
200                 205                 210                 215 ccc tac gtg gac gtc acc ttc acc atc atg ata aga aga cga acc ttg      787
Pro Tyr Val Asp Val Thr Phe Thr Ile Met Ile Arg Arg Arg Thr Leu
                220                 225                 230 tac tac ttc ttc aac ctg atc gtc ccg tgc gtg ctg atc tca tcg atg      835
Tyr Tyr Phe Phe Asn Leu Ile Val Pro Cys Val Leu Ile Ser Ser Met
            235                 240                 245 gca ctc ctc ggc ttc aca ctg cca cca gac tcc gga gag aaa ctc aca      883
Ala Leu Leu Gly Phe Thr Leu Pro Pro Asp Ser Gly Glu Lys Leu Thr
        250                 255                 260 ctt gga gtc act att ctt cta tcg ctg acg gtg ttc ctc aac ctg gta      931
Leu Gly Val Thr Ile Leu Leu Ser Leu Thr Val Phe Leu Asn Leu Val
265                 270                 275 gcc gag acc ctg cca cag gtc tcc gac gct atc ccc ctg tta ggg acg      979
Ala Glu Thr Leu Pro Gln Val Ser Asp Ala Ile Pro Leu Leu Gly Thr
280                 285                 290                 295 tac ttc aat tgc atc atg ttc atg gta gcg tcg tct gtg gta ctg act     1027
Tyr Phe Asn Cys Ile Met Phe Met Val Ala Ser Ser Val Val Leu Thr
                300                 305                 310 gtg gtg gta ctc aat tac cac cat cga aca gct gat ata cat gaa atg     1075
Val Val Val Leu Asn Tyr His His Arg Thr Ala Asp Ile His Glu Met
            315                 320                 325 cca cag tgg ata aaa tca gta ttc cta caa tgg ttg cca tgg ata ctg     1123
Pro Gln Trp Ile Lys Ser Val Phe Leu Gln Trp Leu Pro Trp Ile Leu
        330                 335                 340 cga atg tcg agg cca ggg aag aag atc acc agg aag act ata atg atg     1171
Arg Met Ser Arg Pro Gly Lys Lys Ile Thr Arg Lys Thr Ile Met Met
345                 350                 355 aac acg agg atg agg gag ctg gaa ctg aag gag agg tcg tcg aag tcc     1219
Asn Thr Arg Met Arg Glu Leu Glu Leu Lys Glu Arg Ser Ser Lys Ser
360                 365                 370                 375 ttg ctg gcg aat gtt cta gat att gat gat gac ttc aga cac ggc cct     1267
Leu Leu Ala Asn Val Leu Asp Ile Asp Asp Asp Phe Arg His Gly Pro
                380                 385                 390 ccg cct cct aac agt act gcc tcg acc ggg aat ttg gga cct ggg tgc     1315
Pro Pro Pro Asn Ser Thr Ala Ser Thr Gly Asn Leu Gly Pro Gly Cys
```

-continued

```
                395                 400                 405
tca ata ttc cgc acg gat ttc cgt cgg tcg ttc gtc cgt ccg tcc acg    1363
Ser Ile Phe Arg Thr Asp Phe Arg Arg Ser Phe Val Arg Pro Ser Thr
        410                 415                 420 atg gaa gac gtg ggc ggc ggg ctg ggt agc cac cat cgc gag ctg cac    1411
Met Glu Asp Val Gly Gly Gly Leu Gly Ser His His Arg Glu Leu His
425                 430                 435 ctc ata ctg aga gag ctg cag ttc atc acg gcc agg atg aag aag gct    1459
Leu Ile Leu Arg Glu Leu Gln Phe Ile Thr Ala Arg Met Lys Lys Ala
440                 445                 450                 455 gat gag gaa gcc gag ctg atc agc gac tgg aag ttt gct gcg atg gtt    1507
Asp Glu Glu Ala Glu Leu Ile Ser Asp Trp Lys Phe Ala Ala Met Val
                460                 465                 470 gtt gat agg ttt tgc ctg ttc gtg ttc aca ctt ttc aca atc atc gcg    1555
Val Asp Arg Phe Cys Leu Phe Val Phe Thr Leu Phe Thr Ile Ile Ala
            475                 480                 485 aca gta gct gtc ctg tta tcg gca ccg cat atc atc gtg caa             1597
Thr Val Ala Val Leu Leu Ser Ala Pro His Ile Ile Val Gln
        490                 495                 500
```

| | |
|---|---|
| tgaaccaacc actgagccgg caactccggc gcatgaatga gagaaataat tattagatcg | 1657 |
| ccgatttgta attataattg ataatgtaat taaattaaat acgtggttga aacgcacacg | 1717 |
| tctccataac aaagtcttaa gacattaaat tatgataaat ttacatattg tagttaagtc | 1777 |
| gagtgttgat ggaaatttta gccggcgcaa ggagtttcgt gaaggtctgt atatatttt | 1837 |
| tcttattgtt gtatattgta tcgttgttca tgttttcttt caggaagtga gctttgtact | 1897 |
| gtttgtttct tcgatggcag gtgcacttca gttcaggctg aaatttccat taacatttat | 1957 |
| ttaaacaaat gtgatgttga ctaggatgtt atacagataa atgttgacgt gtataatttg | 2017 |
| ttaaaataaa caatattaat tactattact aaacgatatt ataaacgaag tactaacgag | 2077 |
| ggttacttta atgggaagaa cgctaagctg cacagagtt gcattaattt gaaaaagaa | 2137 |
| attacggaaa aagtttatt gaaaattgaa cttttggaa ggaaagtaac gtttgatcaa | 2197 |
| aaagtttgt aaaacgaaag ttcggttctg cgccaatact ggaattaaaa ttctcgtaaa | 2257 |
| tattagggaa aagaaggtcc tttaaaacaa aagatttgaa ccggcatcct ttttacaagt | 2317 |
| aatgagggat cacagatgat gacaaaaaac cttagggtat ataagtaatg tacataatgg | 2377 |
| atcaaatatc ggtagagtca agaatagtta acgatttaag attattccat tcgatattaa | 2437 |
| aattcgatta gcgattgtcg ctgcgtctac tttgatacat atcgatttga atcgatattg | 2497 |
| tataaattta gatagatcgg acattagtaa tgagtatgga cgttttaatt tttaaaaaag | 2557 |
| aatgtactac gaagattaaa tccaggaatt gttaaacagt tatggaattg ataagaaatc | 2617 |
| aacaattaat acggaaccaa aggtagacta ggtgtagcat caggagattg aattaaaaca | 2677 |
| taaattagga ccgacttaaa tggaacttgc gagtgtattg ataacttttt aatttaaaaa | 2737 |
| ctcattgtcg attaaatgga gaataacttt tgatctctcg tatcgataaa tgctcactta | 2797 |
| actatcgata gcgtaatatt ataactgtta gtatatcgat atgggagtaa gtcactagca | 2857 |
| tcagaaatag tcattaatta ggaatcggtt tgtgttaatg ttatgcttag cgaaaatatt | 2917 |
| acaatgctgt tgatatcact aaccatcacg taaccatatt gataaaatgt aaatacagaa | 2977 |
| tattgcggtg tgtatttgta tataaatttt agaaaaaaaa aaaaaaaaaa aactcgagag | 3037 |
| tacttctaga gcggccgcgg gcccatcgat tttccacccg ggtggggtac caggtaagtg | 3097 |
| tacccaattc gc | 3109 |

-continued

```
<210> SEQ ID NO 6
<211> LENGTH: 501
<212> TYPE: PRT
<213> ORGANISM: Heliothis virescens

<400> SEQUENCE: 6

Met Ala Pro Met Leu Ala Ala Leu Ala Leu Leu Ala Leu Leu Pro Val
  1               5                  10                  15

Ser Glu Gln Gly Pro His Glu Lys Arg Leu Leu Asn Ala Leu Leu Ala
             20                  25                  30

Asn Tyr Asn Thr Leu Glu Arg Pro Val Ala Asn Glu Ser Glu Pro Leu
         35                  40                  45

Glu Val Arg Phe Gly Leu Thr Leu Gln Gln Ile Ile Asp Val Asp Glu
     50                  55                  60

Lys Asn Gln Leu Leu Ile Thr Asn Ile Trp Leu Ser Leu Glu Trp Asn
 65                  70                  75                  80

Asp Tyr Asn Leu Arg Trp Asn Asp Ser Glu Tyr Gly Gly Val Lys Asp
                 85                  90                  95

Leu Arg Ile Thr Pro Asn Lys Leu Trp Lys Pro Asp Val Leu Met Tyr
            100                 105                 110

Asn Ser Ala Asp Glu Gly Phe Asp Gly Thr Tyr Gln Thr Asn Val Val
        115                 120                 125

Val Arg Ser Gly Gly Ser Cys Leu Tyr Val Pro Pro Gly Ile Phe Lys
    130                 135                 140

Ser Thr Cys Lys Met Asp Ile Ala Trp Phe Pro Phe Asp Asp Gln His
145                 150                 155                 160

Cys Asp Met Lys Phe Gly Ser Trp Thr Tyr Asp Gly Asn Gln Leu Asp
                165                 170                 175

Leu Val Leu Lys Asp Glu Ala Gly Gly Asp Leu Ser Asp Phe Ile Thr
            180                 185                 190

Asn Gly Glu Trp Tyr Leu Ile Gly Met Pro Gly Lys Lys Asn Thr Ile
        195                 200                 205

Thr Tyr Ala Cys Cys Pro Glu Pro Tyr Val Asp Val Thr Phe Thr Ile
    210                 215                 220

Met Ile Arg Arg Arg Thr Leu Tyr Tyr Phe Phe Asn Leu Ile Val Pro
225                 230                 235                 240

Cys Val Leu Ile Ser Ser Met Ala Leu Leu Gly Phe Thr Leu Pro Pro
                245                 250                 255

Asp Ser Gly Glu Lys Leu Thr Leu Gly Val Thr Ile Leu Leu Ser Leu
            260                 265                 270

Thr Val Phe Leu Asn Leu Val Ala Glu Thr Leu Pro Gln Val Ser Asp
        275                 280                 285

Ala Ile Pro Leu Leu Gly Thr Tyr Phe Asn Cys Ile Met Phe Met Val
    290                 295                 300

Ala Ser Ser Val Val Leu Thr Val Val Val Leu Asn Tyr His His Arg
305                 310                 315                 320

Thr Ala Asp Ile His Glu Met Pro Gln Trp Ile Lys Ser Val Phe Leu
                325                 330                 335

Gln Trp Leu Pro Trp Ile Leu Arg Met Ser Arg Pro Gly Lys Lys Ile
            340                 345                 350

Thr Arg Lys Thr Ile Met Met Asn Thr Arg Met Arg Glu Leu Glu Leu
        355                 360                 365

Lys Glu Arg Ser Ser Lys Ser Leu Leu Ala Asn Val Leu Asp Ile Asp
    370                 375                 380
```

```
Asp Asp Phe Arg His Gly Pro Pro Pro Asn Ser Thr Ala Ser Thr
385                 390                 395                 400

Gly Asn Leu Gly Pro Gly Cys Ser Ile Phe Arg Thr Asp Phe Arg Arg
                405                 410                 415

Ser Phe Val Arg Pro Ser Thr Met Glu Asp Val Gly Gly Gly Leu Gly
            420                 425                 430

Ser His His Arg Glu Leu His Leu Ile Leu Arg Glu Leu Gln Phe Ile
        435                 440                 445

Thr Ala Arg Met Lys Lys Ala Asp Glu Glu Ala Glu Leu Ile Ser Asp
    450                 455                 460

Trp Lys Phe Ala Ala Met Val Val Asp Arg Phe Cys Leu Phe Val Phe
465                 470                 475                 480

Thr Leu Phe Thr Ile Ile Ala Thr Val Ala Val Leu Leu Ser Ala Pro
                485                 490                 495

His Ile Ile Val Gln
            500

<210> SEQ ID NO 7
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)
<223> OTHER INFORMATION: n means i

<400> SEQUENCE: 7
gaygtngayg araaraayca                                              20

<210> SEQ ID NO 8
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (9)
<223> OTHER INFORMATION: n means i

<400> SEQUENCE: 8
cyytcrtcng crctrttrta                                              20

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
gcgaattcac caccatgaaa aatgcacaac tg                                32

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgagacaata atatgtggtg cctcgag                                      27
```

```
<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
gcaagcttac caccatggga ggtagagcta gacgctcgca c                           41

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
gcctcgagcg acaccatgat gtgtggcgc                                         29

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
gcaagcgccg ctatggcccc tatgttg                                           27

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
ttgcacgatg atatgcggtg cctcgagcg                                         29
```